United States Patent
Olsson

[11] Patent Number: 5,979,515
[45] Date of Patent: Nov. 9, 1999

[54] ASEPTIC TRANSFER

[75] Inventor: Bert-Åke Olsson, Strängnäs, Sweden

[73] Assignee: Astra Aktiebolag, Sodertalje, Sweden

[21] Appl. No.: 09/098,090

[22] Filed: Jun. 16, 1998

Related U.S. Application Data

[62] Division of application No. 08/718,307, Sep. 30, 1996, Pat. No. 5,799,464.

[30] Foreign Application Priority Data

Sep. 8, 1995 [SE] Sweden ................................. 9503102

[51] Int. Cl.$^6$ ...................................................... B65B 1/04
[52] U.S. Cl. ............................... 141/231; 141/91; 141/98
[58] Field of Search .......................... 141/231, 63, 64, 141/93, 97, 91, 98

[56] References Cited

U.S. PATENT DOCUMENTS

| | | | |
|---|---|---|---|
| 5,332,013 | 7/1994 | Sugita et al. ............................. | 141/98 |
| 5,417,255 | 5/1995 | Sanfilippo et al. ....................... | 141/1 |
| 5,799,464 | 9/1998 | Olsson .................................... | 53/425 |
| 5,810,060 | 9/1998 | Bolz et al. ............................... | 141/97 |

Primary Examiner—David J. Walczak
Assistant Examiner—Peter deVore
Attorney, Agent, or Firm—White & Case LLP

[57] ABSTRACT

A transfer device for aseptic and automatic transfer of filled, unsealed pharmaceutical containers (2) which comprises a transport vehicle (11) with a vertically adjustable platform (12) supporting a transportable and sealable chamber (1). The chamber (1) comprises an upper part (8) provided with a protective-gas inlet (7), a lower part (9) provided with a frame (13) for supporting the containers (2), a closable opening (14), and an intermediate, substantially horizontal flow distributor (10).

4 Claims, 1 Drawing Sheet

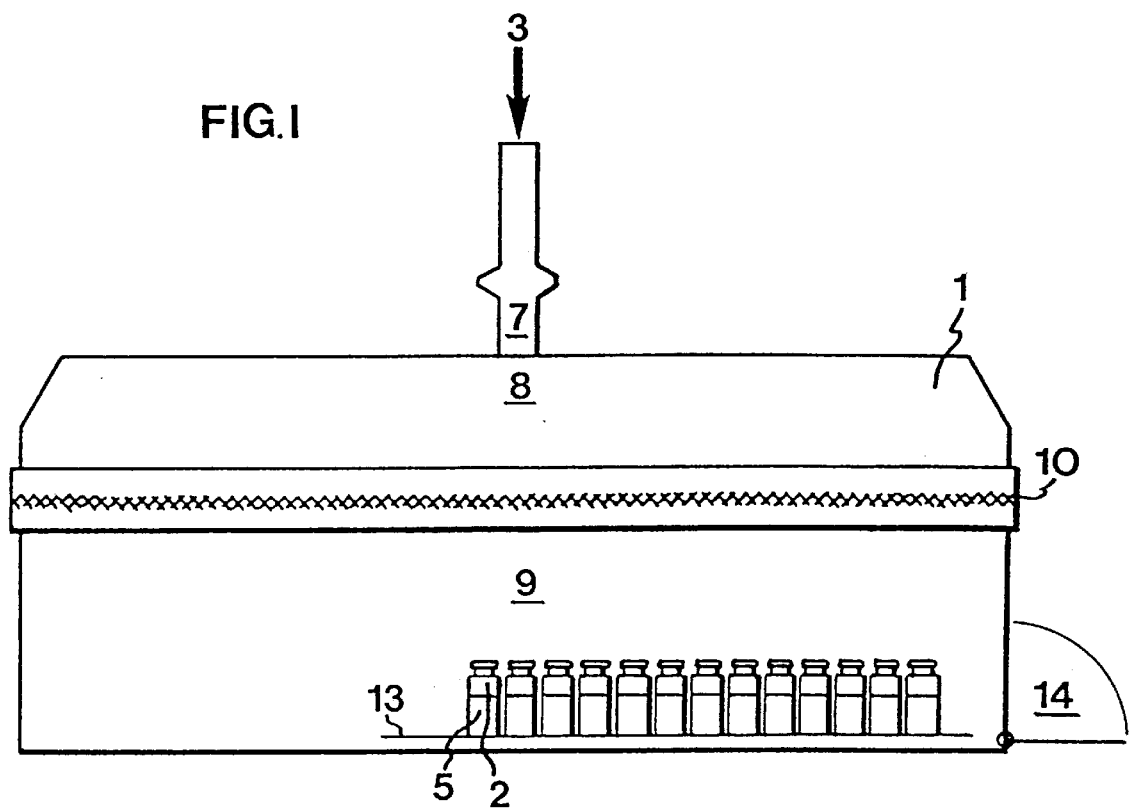
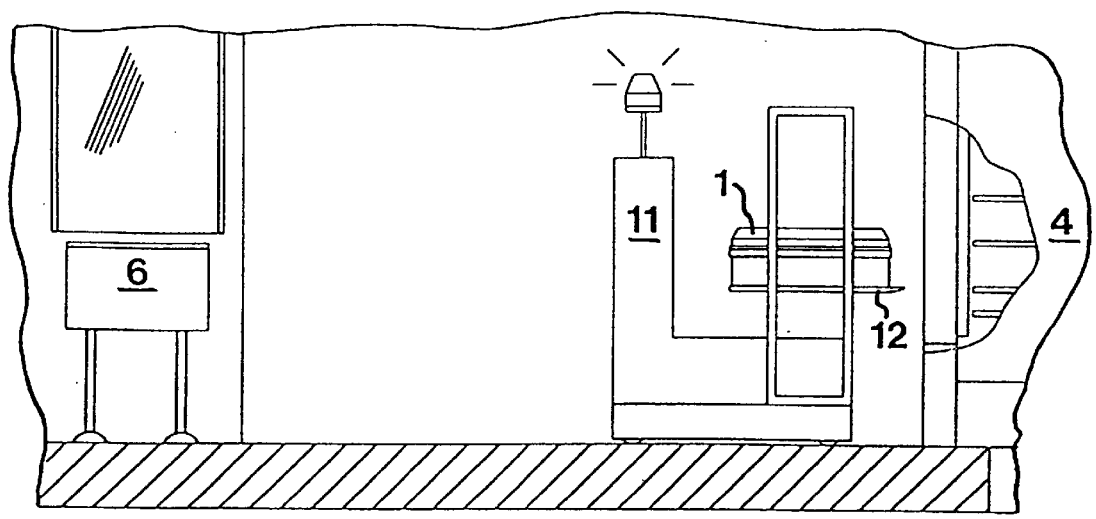

ASEPTIC TRANSFER

This is a divisional of application Ser. No. 08/718,307, filed Sep. 30, 1996, U.S. Pat. No. 5,799,464.

BACKGROUND OF THE INVENTION

The present invention relates to a method and a device for aseptic and automatic transfer of unsealed pharmaceutical containers, which have been aseptically filled with a pharmaceutical preparation, from a filling device to a subsequent unit.

As regards pharmaceutical formulations, it has always been a serious problem to maintain the required hygienic conditions during the transfer of solutions or substances aseptically filled in pharmaceutical containers from a filling machine to the subsequent process step, e.g. a freeze-drying step. During such a transfer, the hygienic conditions should always be the same as during the filling and freeze-drying process. Also, the authorities will in all probability tighten the requirements for higher purity levels in this technique area.

DESCRIPTION OF THE PRIOR ART

It is known to manually transfer trays with unsealed or partly sealed containers aseptically filled with pharmaceutical preparations from a filling machine to a freeze-drier. In such a case, the pharmaceutical preparation in the container is exposed to the surrounding air and the particles and microorganisms therein, and the hygiene class of the preparation is adversely affected. Preparations sensible to air are difficult to handle in such a manner.

In an automatic transfer process, it is also known to use a large shelf device and air sterilised by filtration as protective gas. However, the equipment required for such use takes up quite a lot of space, and the time required is too long and therefore harmful for the preparation.

EP 440 042 (Capsulite Spa) is related to a process and a device for the sterilisation of plants for filling e.g. pharmaceutical bottles by using a nitrogen injection system. The purpose of this device is to clean the filling plant at the end of a production cycle and to maintain a pressure with inert gas therein until the subsequent production cycle starts. The nitrogen injection is a complement to the injection of cleaning water and steam.

JP 03216174 (Iwatani International Corp.) relates to an aseptic freezing device, in which liquid nitrogen is used for freezing a pharmaceutical product. The liquid nitrogen is passed through a filter in the freezing chamber, such that microorganisms and dust are separated. The cleaned nitrogen is utilised for freezing the product.

However, there is still a need for a process for aseptic transfer of aseptically filled pharmaceutical containers, which enables the highest hygiene class to be maintained throughout the transfer process and which requires a relatively small space.

SUMMARY OF THE INVENTION

The object of the present invention is to eliminate the above-mentioned problems.

This object is achieved by a method which is of the type described by way of introduction and which is characterised by the steps of a) introducing a sterile inert protective gas into a transportable chamber, b) inserting the chamber into the filling device, c) introducing the pharmaceutical containers into the chamber and closing the chamber, and d) transporting the chamber to the subsequent unit, in which the pharmaceutical containers are removed from the chamber, said protective gas being continuously and evenly distributed in steps b)–d) over the unsealed pharmaceutical containers.

The inventive object is also achieved by a transfer device for aseptic and automatic transfer of unsealed pharmaceutical containers, which have been aseptically filled with a pharmaceutical preparation, from a filling device to a subsequent unit, said transfer device comprising a controllable transport vehicle, a vertically adjustable platform provided thereon and a transportable and hermetically sealable chamber provided on the platform and holding the pharmaceutical containers during the transfer, said transfer device being characterised in that the chamber comprises a) an upper part provided with a protective-gas inlet, b) a lower part provided with a frame for keeping the pharmaceutical containers during the transfer and with a closable opening for the introduction and removal of the pharmaceutical containers, said upper part and said lower part being separated by an intermediate, substantially horizontal flow distributor for even distribution of protective gas from the upper part over the pharmaceutical containers in the lower part.

The present invention is advantageous in that it enables an improved transfer of filled pharmaceutical containers, which is aseptically performed while maintaining the hygienic class required. Further, the total equipment costs for the transfer process are less than for a static process, and the work load of the operators is minimised. Another advantage is that several subsequent units, e.g. freeze-driers, can be served.

None of the references cited above refers to a method for automatic and aseptic transfer by using a protective gas evenly distributed over the aseptically filled containers in a transportable chamber.

The present invention will now be described in more detail with reference to the accompanying drawings, in which FIG. 1 is a cross-sectional view of a chamber used in the process according to the invention, and FIG. 2 is a cross-sectional view of an inventive transport device in operation.

DESCRIPTION OF AN EMBODIMENT

Referring to FIG. 1, the transfer device according to the invention comprises a transportable chamber 1, which is sealable and has an upper part 8 provided with a protective-gas inlet 7 and acting as a pressure-equalising space, as well as a lower part 9 provided with a frame 13 for keeping pharmaceutical containers 2 during the transfer thereof. Further, the lower part 9 is provided with a closable opening 14 for the introduction and removal of the pharmaceutical containers 2. The bottom of the lower part 9 is also provided with slits (not shown) for effluent protective gas in order to allow continuous introduction of the protective gas into the chamber 1, thereby avoiding overpressure therein. The upper part 8 and the lower part 9 are separated by an intermediate, substantially horizontal flow distributor 10 enabling even introduction of protective gas 3 from the upper part 8 over the orifices of the pharmaceutical containers 2 in the lower part 9. The flow distributor 10 comprises perforated plates and a filter sandwiched therebetween. The flow distributor 10 serves to distribute the protective-gas flow evenly over the whole area of the lower part 9, in which the containers 2 are located. This is achieved by the pressure reduction obtained in the flow distributor 10.

Preferably, the whole chamber 1 is sterilised, e.g. in an autoclave, before use.

At the bottom of the lower part 9, there is also provided a ball screw controlled pulling device (not shown) for the introduction and the removal of the containers 2 to and from the chamber 1. The frame 13, which also is located at the bottom of the lower part 9 and is connected to the pulling device, is adapted to keep the number of containers 2 required during the transfer. The number of containers 2 to be transferred depends, inter alia, on the type of pharmaceutical container 2 at issue. In one embodiment of the present invention, 400 vials are kept by the frame 13 during the transfer.

When liquid preparations are to be transferred, it is very important to keep the surface of the preparation as immovable as possible, and all kinds of splashing should be avoided.

A closable opening 14 of the chamber 1 is preferably located in one of the side walls of the lower part 9. The opening 14 can be opened and closed by means of a door.

The protective gas 3 is sterilised by filtration, e.g. with the aid of a particle filter, before it is introduced into the upper part 8 of the chamber 1. The protective gas 3 can be continuously introduced from a protective-gas supply connected to the chamber 1. Preferably, the protective gas 3 is introduced vertically through an opening at the top of the upper part 8.

The protective gas 3 is preferably nitrogen, a noble gas, or a mixture thereof. In a preferred embodiment, nitrogen is used as protective gas.

The filter of the flow distributor 10 is a commercially available PPM-PPF filter made of sintered plastic beads having an average diameter of about 3 mm. The filter capacity is about 100 particles per foot$^3$, i.e. about 3.5 particles per liter. However, other filters with a similar capacity and construction can also be used.

The pharmaceutical containers 2 to be transferred from the filling device 6 to the subsequent unit 4 in accordance with the inventive method preferably are pharmaceutical vials, ampoules or bottles, or other similar pharmaceutical containers. The containers 2 can be made of any conventional and suitable material, but are normally made of glass or plastic.

Further, the containers 2 are kept unsealed after the filling operation. By the expression "unsealed", as used throughout the description and the claims, is meant that the preparation in each container 2 is in contact with the surrounding atmosphere. However, the containers 2 can be provided with conventional plugs of different shapes in such a manner that the containers 2 are partly sealed.

When the subsequent unit 4 is a freeze-drier, the containers 2 can be provided with a plug having openings horizontally located in relation to the transfer direction to allow the evaporation of vapour and/or gaseous components from the pharmaceutical product in the subsequent freeze-drying step. After such evaporation, the containers 2 holding the freeze-dried pharmaceutical preparation 5 are hermetically sealed.

The pharmaceutical preparation 5 in the unsealed containers 2 to be aseptically transferred can be any liquid or solid preparation. In a preferred embodiment, the pharmaceutical preparation is a solution of omeprazol, which is sensitive to carbon dioxide.

By the expression "filled", used throughout the description and the claims, is meant that the pharmaceutical preparation has been added to the container 2 in the filling device up to an optional level in the container 2.

The dimensions of the chamber 1 are not critical, but it is important that there is enough space between the container orifices and the flow distributor 10 in the lower part 9.

Further, the containers 2 and the preparation do not necessarily have to be pharmaceutical. Other types of containers filled with liquid or solid chemical preparations requiring hygienic or non-oxidisable transfer or storage conditions can also be treated by the process according to the present invention.

Referring to FIG. 2, the transfer device comprising the chamber 1 also includes a controllable transport vehicle 11 and a vertically adjustable platform 12 provided thereon. The chamber 1 is in turn provided on the platform 12, and is transferred from the filling device 6 to the subsequent unit 4, preferably consisting of one or more freeze-driers.

The transport vehicle 11 preferably is a minitruck controlled by a laser-guided control system controlling the minitruck in the operating area thereof. The control signals are transferred by a radio link, and the system considerably facilitates changes in the movement pattern of the minitruck.

The total process time for the transfer is less than 20 min, preferably about 2.5 min.

The present invention will now be further elucidated with the aid of the following Example of a transfer process for Omeprazol.

EXAMPLE

In a transfer room, two minitrucks are operated simultaneously, each having a chamber 1 for the transport of containers 2. The chamber has a length of 0,75 m, a width of 0,4 m and a height of 0,35 m. The height of the upper part 8 is 0,15 m and the height of the lower part is 0,20 m. The total thickness of the perforated plates and the PPM-PPF filter sandwiched therebetween is 1 cm. The perforated plates have a thickness of 1 mm, respectively, and are made of stainless steel. The hole diameter thereof is 3 mm placed in a triangle with a width of 5 mm.

After having been filled with nitrogen, each chamber 1 is inserted at two different sites on the same height level in a filling machine. 400 pharmaceutical vials with an inner diameter of 21 mm and a height of 45 mm, which have been aseptically filled with a solution of omeprazol to a degree of about 25% of the vial and provided with partly sealing plugs, are introduced through the opening 14 of each chamber 1, which is then closed and conveyed by the minitruck while nitrogen 3 is continuously introduced into it at a flow rate of about 500 l/min. The chambers 1 are transferred to three different freeze-dryers 4, each consisting of 144 storage locations arranged on twelve shelf levels with three positions in width and four positions in length on each level.

The vertically adjustable platform 12 is guided by the programmed control system of the minitrucks to insert the vials 2 in the right positions in the freeze-drier 4.

The vials 2 are withdrawn from the chamber 1 to the freeze-drier, still under the aseptic conditions required.

Thus, the whole transfer of the containers 2 from the filling machine 6 to the subsequent freeze-drier is performed completely automatically and under the hygiene conditions required. The total process time is about 2.5 min.

I claim:

1. Transfer device for aseptic and automatic transfer of unsealed pharmaceutical containers (2), which have been aseptically filled with a pharmaceutical preparation (5), from a filling device (6) to a subsequent unit (4), said transfer device comprising a transport vehicle (11), a vertically adjustable platform (12) provided thereon and a transportable and sealable chamber (1) provided on the platform (12) and holding the pharmaceutical containers (2) during the transfer, characterised in that the chamber (1) comprises a) an upper part (8) provided with a protective-gas inlet (7), b) a lower part (9) provided with a frame (13) for keeping the pharmaceutical containers (2) during the transfer and with a closable opening (14) for the introduction and removal of the pharmaceutical containers (2), said upper part (8) and said lower part (9) being separated by an intermediate, substantially horizontal flow distributor (10) for even distribution of protective gas (3) from the upper part (8) over the pharmaceutical containers (2) in the lower part (9).

2. Transfer device according to claim 1, wherein the flow distributor (10) of the chamber (1) comprises perforated plates and a filter made of sintered plastic beads sandwiched therebetween.

3. Transfer device according to claim 1, wherein the frame (13) of the chamber (1) is capable of keeping about 400 pharmaceutical containers (2) during a transfer.

4. Transfer device according to claim 1, wherein the transfer of the pharmaceutical containers (2) in the chamber (1) is controlled by a laser-guided control system for the transport vehicle (11).

* * * * *